US009433913B2

(12) United States Patent
Pfefferle et al.

(10) Patent No.: US 9,433,913 B2
(45) Date of Patent: *Sep. 6, 2016

(54) CATALYTIC ISOBUTANE ALKYLATION

(71) Applicant: PRECISION COMBUSTION, INC., North Haven, CT (US)

(72) Inventors: William C Pfefferle, Madison, CT (US); Shahrokh Etemad, Trumbull, CT (US)

(73) Assignee: PRECISION COMBUSTION, INC., North Haven, CT (US)

( * ) Notice: Subject to any disclaimer, the term of this patent is extended or adjusted under 35 U.S.C. 154(b) by 469 days.

This patent is subject to a terminal disclaimer.

(21) Appl. No.: 14/059,911

(22) Filed: Oct. 22, 2013

(65) Prior Publication Data

US 2014/0044613 A1 Feb. 13, 2014

Related U.S. Application Data

(63) Continuation of application No. 11/726,106, filed on Mar. 21, 2007, now Pat. No. 8,603,407.

(51) Int. Cl.
*B01J 19/00* (2006.01)
*B01J 19/24* (2006.01)
*C07C 2/54* (2006.01)
*C07C 2/56* (2006.01)
*C07C 2/58* (2006.01)
*B01J 12/00* (2006.01)
*B01J 16/00* (2006.01)

(52) U.S. Cl.
CPC ............ *B01J 16/005* (2013.01); *B01J 12/007* (2013.01); *B01J 19/2475* (2013.01); *C07C 2/58* (2013.01); *C07C 2529/068* (2013.01)

(58) Field of Classification Search
CPC ........ B01J 12/00; B01J 12/007; B01J 16/00; B01J 16/005; B01J 19/00; B01J 19/24; B01J 19/2415; B01J 19/244; B01J 19/2475; C07C 2/54–2/58; C07C 2529/04; C07C 2529/06–2529/068
See application file for complete search history.

(56) References Cited

U.S. PATENT DOCUMENTS

| 3,893,942 A | 7/1975 | Yang |
| 4,008,291 A | 2/1977 | Zabransky |
| 5,583,240 A | 12/1996 | Asher |
| 6,238,815 B1 | 5/2001 | Skala |

(Continued)

FOREIGN PATENT DOCUMENTS

| WO | WO02074701 A1 | 9/2002 |
| WO | WO2009023050 A2 | 2/2009 |

OTHER PUBLICATIONS

A.L. Tonkovich et al., "Experimental Investigations of Inorganic Membrane Reactors: A Distributed Feed Approach for Partial Oxidation Reactions," Chemical Engineering Science, vol. 51, No. 5 (1996), pp. 789-806.

(Continued)

*Primary Examiner* — Natasha Young

(57) ABSTRACT

A novel catalytic reactor is provided for controlling the contact of a limiting reactant with a catalyst surface. A first flow vessel defines an interior surface and an exterior surface, and the interior surface has a catalyst deposited on at least a portion thereof. A second flow vessel is positioned within the first flow vessel and the second flow vessel defines a porous surface designed to deliver a fluid uniformly to at least a portion of the interior surface of the first flow vessel.

10 Claims, 2 Drawing Sheets

(56) References Cited

U.S. PATENT DOCUMENTS

| | | |
|---|---|---|
| 6,818,189 B1 | 11/2004 | Adris |
| 6,838,064 B2 | 1/2005 | Sakai |
| 6,977,064 B1 | 12/2005 | Adris |
| 8,603,407 B2 * | 12/2013 | Pfefferle ................ B01J 12/007 422/198 |
| 2004/0229752 A1 | 11/2004 | Long |
| 2005/0166456 A1 | 8/2005 | Brundage |
| 2005/0245782 A1 | 11/2005 | Pfefferle |
| 2005/0250972 A1 | 11/2005 | Pfefferle |
| 2005/0256358 A1 | 11/2005 | Wang |
| 2006/0067861 A1 | 3/2006 | Tonkovich |
| 2007/0270623 A1 | 11/2007 | Merrill |

OTHER PUBLICATIONS

T. F. Edgar, et al., "Process Control," Perry's Chemical Engineers' Handbook, McGraw-Hill, 7th ed., Sec. 8, R. H. Perry & D. W. Green, eds., 1997, available on-line Mar. 1, 2001, at www.knovel.com.

V Meille, "Review on Methods to Deposit Catalysts on Structured Surfaces," Applied Catalysis A: General, vol. 315 (2006), pp. 1-17.

* cited by examiner

CATALYTIC ISOBUTANE ALKYLATION

CROSS-REFERENCE TO RELATED APPLICATION

This application is a continuation of U.S. patent application Ser. No. 11/726,106, now U.S. Pat. No. 8,603,407, filed Mar. 21, 2007, which is incorporated by reference herein in its entirety.

BACKGROUND OF THE INVENTION

1. Field of the Invention

The present invention relates to a method for catalytic isobutane alkylation. More particularly, the present invention is directed to a catalytic isobutane alkylation process that is advantageous for the alkylation of isobutane or benzene, as well as other compounds.

2. Description of the Related Art

Isobutane alkylation by reaction with an olefin is an important refinery process producing a high-octane alkane hydrocarbon product used to produce high-octane gasoline of low aromatic content. Commercial alkylation processes rely on use of either hydrogen fluoride or sulfuric acid catalyst systems. Unfortunately, both systems pose both environmental and safety hazards.

Hydrogen fluoride is an extremely toxic gas and even very small leaks are both a potentially lethal hazard for plant personnel and an area-wide health hazard. On the other hand, sulfuric acid is a burn hazard and the organics-contaminated spent acid is a toxic material that, if burned, creates sulfur oxide fumes. Consequently, it is an object of the present invention to provide a more environmentally benign alkylation process that could be used for alkylation of butane and aromatic compounds such as benzene. It is another object of the present invention to provide solid catalyst systems for use in heterogeneous fixed bed reactors.

With the development of synthetic zeolites, solid catalysts with a high activity for isobutane alkylation have become available. As is known in the art, zeolitic catalysts active for commercial alleviation processes also are active for olefin polymerization, a reaction that reduces alkylate octane and can produce high molecular weight polymers. Further, because the olefin polymerization reaction tends to be favored over the desired alkylation reaction, a very high ratio of isobutane-to-olefin must be used to reduce the probability of olefin-to-olefin polymerization.

In commercial alkylation processes, polymer formation produces sludge; however, it is merely a nuisance. In contrast, in an alkylation process employing a solid catalyst, polymer formation can block the active sites thereby requiring catalyst regeneration. Moreover, with both conventional and zeolite catalysts, the required high isobutane-to-olefin ratio increases operating cost because the unreacted isobutane must be recovered from the product stream and recycled. Unfortunately, polymer formation on a fixed-bed zeolitic catalyst results in catalyst deactivation in an economically unacceptable short time if operated at the isobutane-to-olefin ratio used in the commercial processes.

Accordingly, it is an object of the present invention to provide a catalytic isobutane alkylation process that overcomes these and other drawbacks associated with known commercial alkylation processes. It is yet another object of the present invention to provide a catalytic isobutane alkylation process that is advantageous regardless of the compound to be alkylated.

DESCRIPTION OF THE INVENTION

It has now been found that using a unique reactor design together with controlled addition of olefin, a nominally constant low olefin concentration can be maintained at the catalyst surface. In isobutane alkylation, for example, the effective isobutane-to-olefin surface ratio can even be greater than a thousand-to-one at feed ratios of ten or twenty-to-one.

Polymer formation on a fixed-bed alkylation catalyst can be reduced to an acceptable level allowing the use of known solid alkylation catalysts at isobutane-to-olefin ratios acceptable in commercial isobutane alkylation. The present invention allows operation even at isobutane-to-olefin ratios lower than those required in current commercial processes. It has now been found that high isobutane ratios on the catalyst surface do not require high isobutane ratios for the feed streams. Although described in terms of isobutane alkylation, the method of the present invention is generic and applies to alkylation of any compound with an olefin and to any reaction where it is desirable to limit concentration of a reactant on a catalytic surface.

DETAILED DESCRIPTION OF THE DRAWINGS

Figure 1:
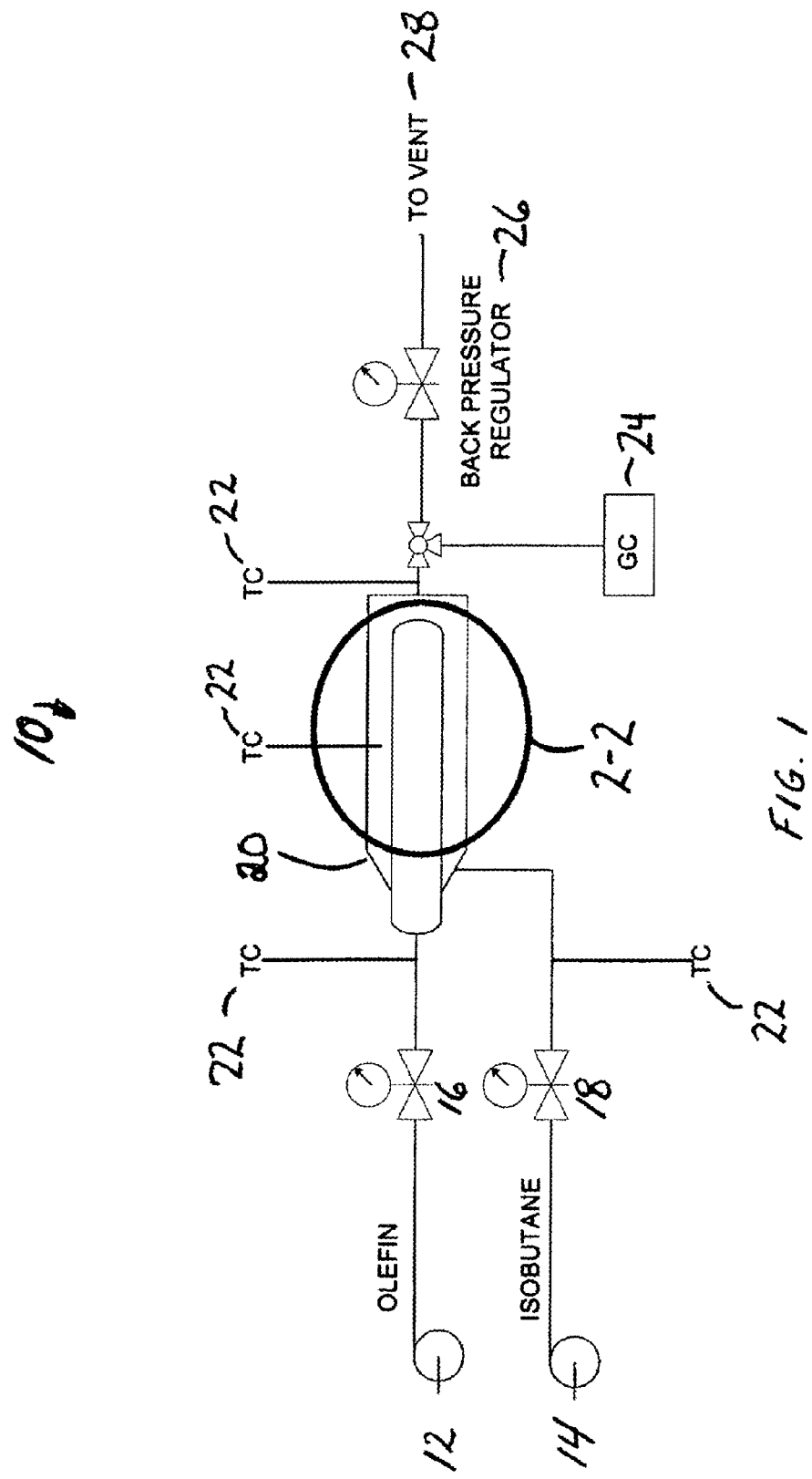
FIG. 1 provides a schematic of an isobutane alkylation system according to the present invention.

Isobutane alkylation system 10 according to the present invention for the alkylation of isobutane is depicted in FIG. 1. System 10 comprises an olefin feed 12 and an isobutane feed 14 controlled by respective flow regulators 16 and 18. The catalytic isobutane alkylation process occurs inside catalytic reactor 20, which reactor is further described with reference to FIG. 2. Four thermocouples 22 and a sample gas chromatograph 24 collect data for further evaluation of the catalytic isobutane alkylation process. Isobutane alkylation system 10 further comprises back pressure regulator 26 and then the products are passed to vent 28.

Figure 2:
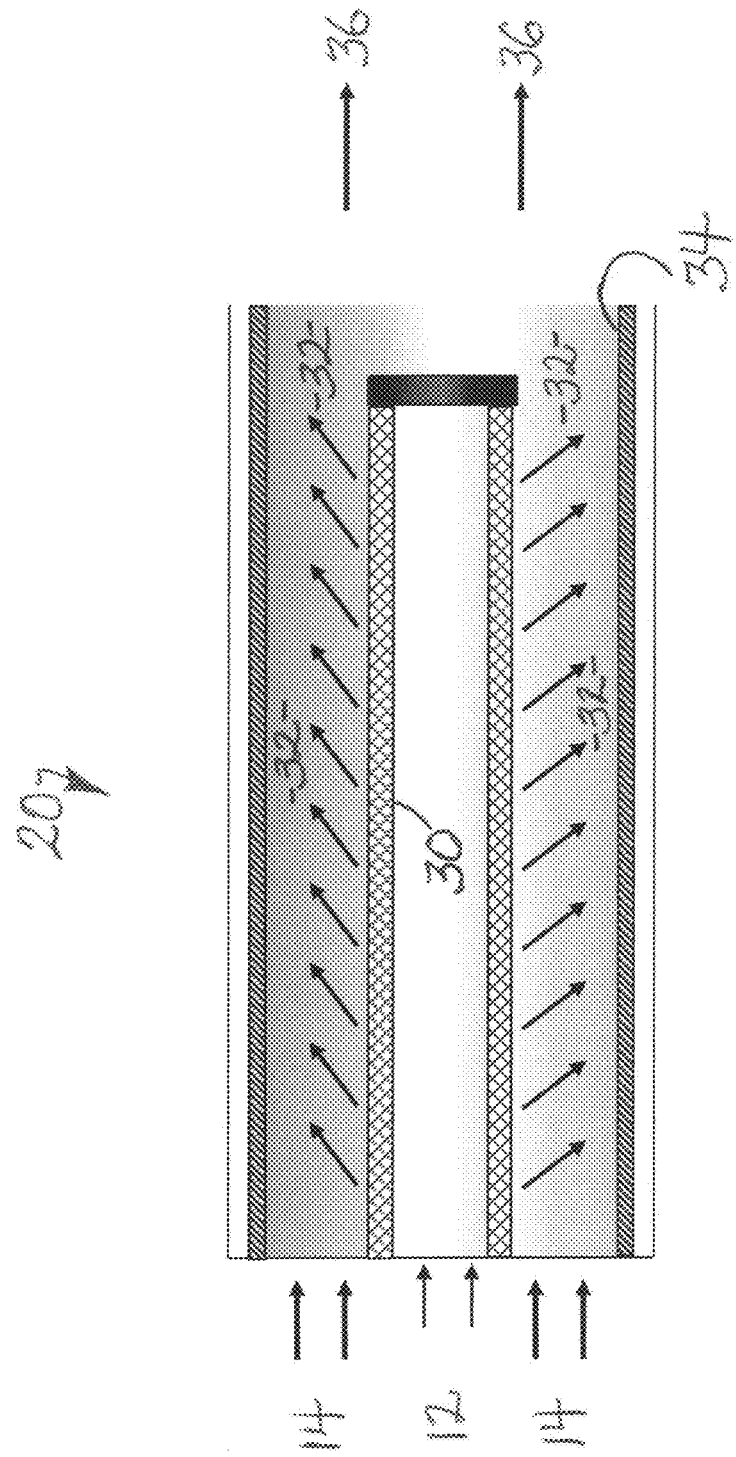
FIG. 2 provides a cross section of the encircled area noted by the designation "2-2" on FIG. 1.

Catalytic reactor 20, as shown in FIG. 2, comprises a porous metal tube 30 that delivers the uniform flow of olefin 12 into the interior 32 of a catalyst coated outer tube 34 through which passes the flow of isobutane 14. Olefin 12 is passed into the porous metal tube 30 at a rate such that the olefin surface concentration at catalyst coated outer tube 34 surface is maintained at a high isobutane-to-olefin ratio. By controlling the olefin feed rate into the porous tube, olefin is injected at a uniform rate over the length of the tube such that mass transfer of olefin to the catalyst surface is limited to a value at which rapid catalytic reaction of olefin with isobutane limits olefin concentration to a desired level. The overall feed rate isobutane to olefin ratio is thus a function of reactor length determined by the cumulative production of alkylate 36.

In the embodiment of the present invention described herein, the term porous tube includes any device for flowing a reactant uniformly into contact with a catalyst surface at a controlled rate. Flat plate designs may be used. The design of FIG. 2 may be used for partial oxidation reactions wherein the flow of oxygen is limited on the surface of an oxidation catalyst to limit heat release. Reaction temperature may be controlled by backside cooling of the reactor in exothermic reactions. For endothermic reactions, reaction temperature can be maintained by backside heating.

Although the invention has been described in considerable detail with respect to the catalytic alkylation of isobutane, it will be apparent that the invention is capable of numerous modifications and variations, apparent to those skilled in the art, without departing from the spirit and scope of the invention.

The invention claimed is:

1. A reactor for the partial oxidation of a hydrocarbon with an oxidant, wherein the reactor provides for controlling the contact of a limiting reactant comprising the oxidant with a catalyst surface, the reactor comprising:
   (a) a first flow vessel defining an interior surface and an exterior surface;
   (b) a catalyst capable of catalyzing the partial oxidation of a hydrocarbon, the catalyst deposited on at least a portion of the interior surface of the first flow vessel;
   (c) a second flow vessel positioned within the first flow vessel wherein the second flow vessel defines a porous surface designed to deliver a limiting reactant comprising an oxidant uniformly over the surface of the partial oxidation catalyst deposited on the interior surface of the first flow vessel; and
   (d) wherein under operative conditions when passing a feed of hydrocarbon between the second flow vessel exterior surface and the first flow vessel interior surface and when passing a feed of oxidant into the second flow vessel, a hydrocarbon-to-oxidant surface ratio at the surface of the catalyst is maintained greater than 50 times a hydrocarbon-to-oxidant feed ratio of the feeds of hydrocarbon and oxidant to the reactor.

2. The reactor of claim 1 wherein the catalyst comprises a precious metal.

3. The reactor of claim 2 wherein the catalyst comprises platinum.

4. The reactor of claim 2 wherein the catalyst comprises rhodium.

5. The reactor of claim 1 wherein the first vessel exterior surface is in contact with a heat transfer fluid.

6. The reactor of claim 1 wherein under operative conditions the hydrocarbon-to-oxidant surface ratio at the surface of the catalyst is greater than 1,000/1 at a feed ratio of hydrocarbon-to-oxidant of 10/1 or 20/1.

7. A reactor for partial oxidation of a hydrocarbon comprising:
   (a) an outer tube defining an outer tube interior surface and an outer tube exterior surface;
   (b) a catalyst capable of catalyzing a partial oxidation of a hydrocarbon, the catalyst deposited on at least a portion of the outer tube interior surface so as to define a catalyst surface;
   (c) a porous metal tube positioned within the outer tube defining a porous metal tube interior surface and a porous metal tube exterior surface and providing a uniform flow rate over the length of the porous metal tube from the porous metal tube exterior surface to the outer tube interior surface; and
   (d) wherein under operative conditions when passing a feed of hydrocarbon between the porous metal tube exterior surface and the outer tube interior surface and when passing a feed of oxidant into the porous metal tube, a hydrocarbon-to-oxidant surface ratio at the surface of the catalyst is maintained greater than 50 times a hydrocarbon-to-oxidant feed ratio of the feeds of hydrocarbon and oxidant to the reactor.

8. The reactor of claim 7 wherein the catalyst comprises a precious metal.

9. The reactor of claim 8 wherein the catalyst comprises platinum or rhodium.

10. The reactor of claim 1 wherein under operative conditions the hydrocarbon-to-oxidant surface ratio at the surface of the catalyst is greater than 1,000/1 at a feed ratio of hydrocarbon-to-oxidant of 10/1 or 20/1.

* * * * *